United States Patent [19]

Hepburn

[11] Patent Number: 4,485,808

[45] Date of Patent: * Dec. 4, 1984

[54] ADJUSTABLE SPLINT

[75] Inventor: George R. Hepburn, Severna Park, Md.

[73] Assignee: Dynasplint Systems, Inc., Baltimore, Md.

[*] Notice: The portion of the term of this patent subsequent to Aug. 9, 2000 has been disclaimed.

[21] Appl. No.: 367,598

[22] Filed: Apr. 12, 1982

[51] Int. Cl.³ .............................................. A61F 5/04
[52] U.S. Cl. ................................................ 128/87 R
[58] Field of Search .................. 128/87 R, 88, 83, 85, 128/80 C, 80 F

[56] References Cited

U.S. PATENT DOCUMENTS 2,661,000 12/1953 Gazeley et al. ........................ 128/88
3,548,817 12/1970 Mittasch ........................... 128/87 R

FOREIGN PATENT DOCUMENTS 830507 3/1960 United Kingdom .............. 128/80 F

Primary Examiner—John D. Yasko
Attorney, Agent, or Firm—Larson and Taylor

[57] ABSTRACT

An adjustable splint assembly comprising a lower strut and an upper strut pivotably connected to said lower strut, one of said struts having at one end a pivotably mounted head portion defining a cam surface, an adjustable biasing means mounted within the other strut and biased into engagement with said cam surface, for applying a quantifiable force tending to approximate said upper and lower struts and means for securing said splint assembly to a limb.

7 Claims, 5 Drawing Figures

ADJUSTABLE SPLINT

BACKGROUND OF THE INVENTION

1. Field of the Invention

This invention relates to an adjustable splint. More particularly, this invention relates to an adjustable splint useful in treating impairments in body joints such as knees, elbows, wrists, fingers, backs and the like from extension contracture, weakness in the supporting musculature, or some other malady inhibiting the integrity of the body joint in accomplishing flexion.

2. Prior Art

People develop extension contractures in the fingers, wrists, elbows, knees and other joints from many and various causes. Weakness, disuse, fractures, surgeries, traumatic injuries, illness and other causes have been known to cause loss of ability to flex the body joint otherwise known as an extension contracture. No device presently exists to reduce extension contractures by adjustable, quantifiable pressure as does the adjustable splint for flexion described herein.

Many splint devices and mechanisms have been designed to be influential at the knee either for support or for mobilizing the knee joint. Illustrative of such devices are those described in U.S. Pat. Nos. 3,055,359; 3,928,872; 3,785,372 and 3,799,159. However, all of these devices are not designed to reduce extension contractures or cannot be tolerated by the patient population for a long enough period to effectively reduce an extension contracture. Moreover, none of the devices offer a satisfactory means for adjusting the pressure exerted by the lateral struts of the splint devices.

OBJECTS OF THE INVENTION

Accordingly, it is an object of the invention to provide an improved splint device for reducing extension contractures about a body joint such as a knee, elbow, finger or wrist.

Another object of the invention is to provide a splint device which will shorten the rehabilitation time of individuals that are bedridden or incapacitated due to extension contractures about a joint.

Yet another object of the invention is to provide a splint device, which allows easy gradual adjustment to the quantifiable force desired on an extremity acting across a body joint.

A further object of the invention is to provide a splint device for incarcerated patients to help obtain a higher level of independence in their activities of daily living, self care and ambulatory activities.

A further object would be to provide an improved splint for providing support to a limb around a body joint such as a knee, elbow, wrist or finger, in cases where muscular weakness exists.

SUMMARY OF THE INVENTION

These and other objects of the invention are obtained by an adjustable splint assembly comprising a lower strut and an upper strut pivotably connected to said lower strut, one of said struts having at one end a pivotably mounted head portion defining a cam surface, an adjustable biasing means mounted within the other strut and biased into engagement with said cam surface, for applying a quantifiable force tending to approximate said upper and lower struts and means for securing said splint assembly to a limb.

In a preferred embodiment the present invention comprises a pair of lower struts and a pair of upper struts, each member of the pair of lower struts being pivotably connected to a member of the pair of upper struts, said members of each pair being spaced apart a distance to accomodate limb parts distal and proximal to the limb joint, at least one of said struts having at one end, a pivotably mounted head portion defining a cam surface, an adjustable biasing means mounted within the strut pivotably connected to said cam surface-containing strut and biased into engagement with said cam surface, for applying a quantifiable force tending to approximate the cam surface containing strut with the adjustable biasing means containing strut and means provided said pair of upper struts and said pair of lower struts for securely holding therebetween said distal and proximals parts of a limb.

BRIEF DESCRIPTION OF THE DRAWINGS

The invention will appear more clearly from the following detailed description when taken in connection with the following drawings which show by way of example a preferred embodiment of the invention.

In the drawings.

DESCRIPTION OF THE PREFERRED EMBODIMENT

Figure 1:
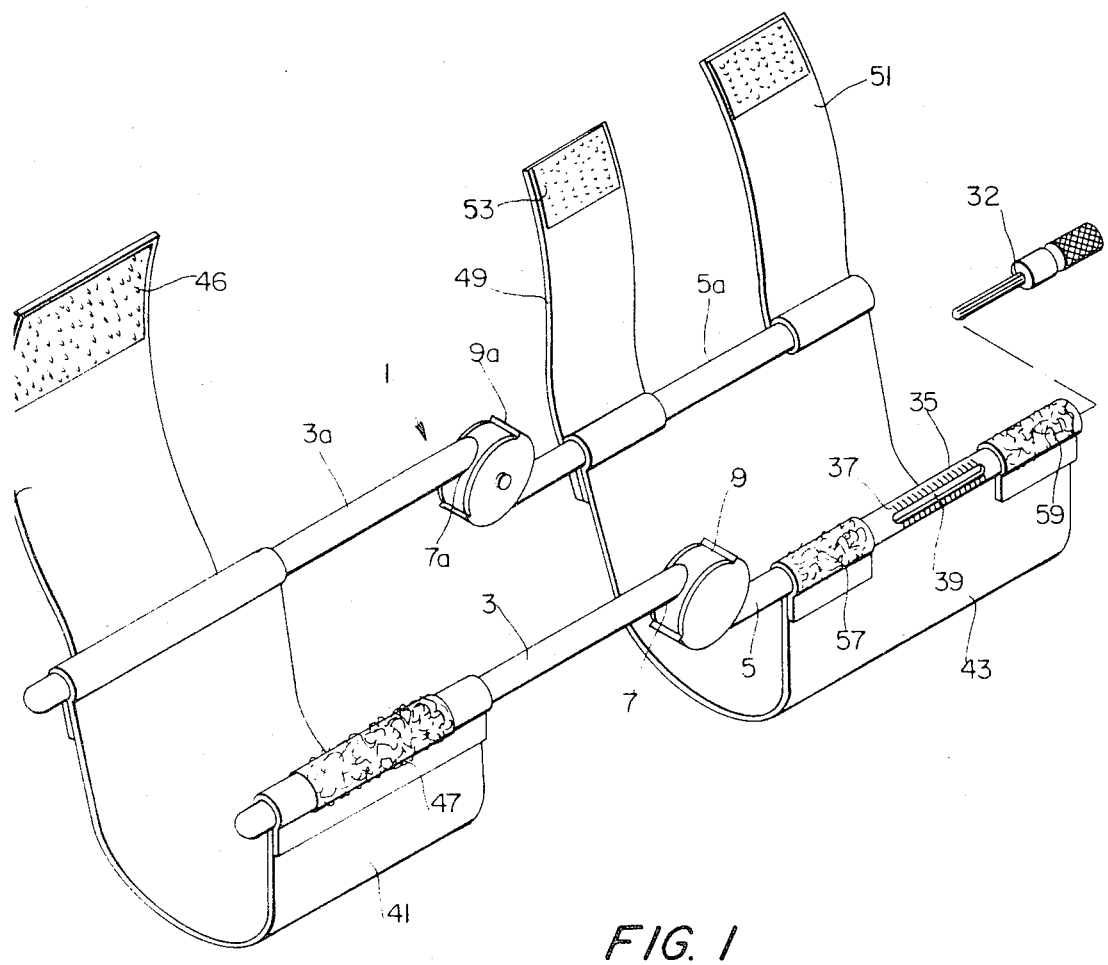
FIG. 1 is a perspective view of the adjustable splint.
Figure 2:
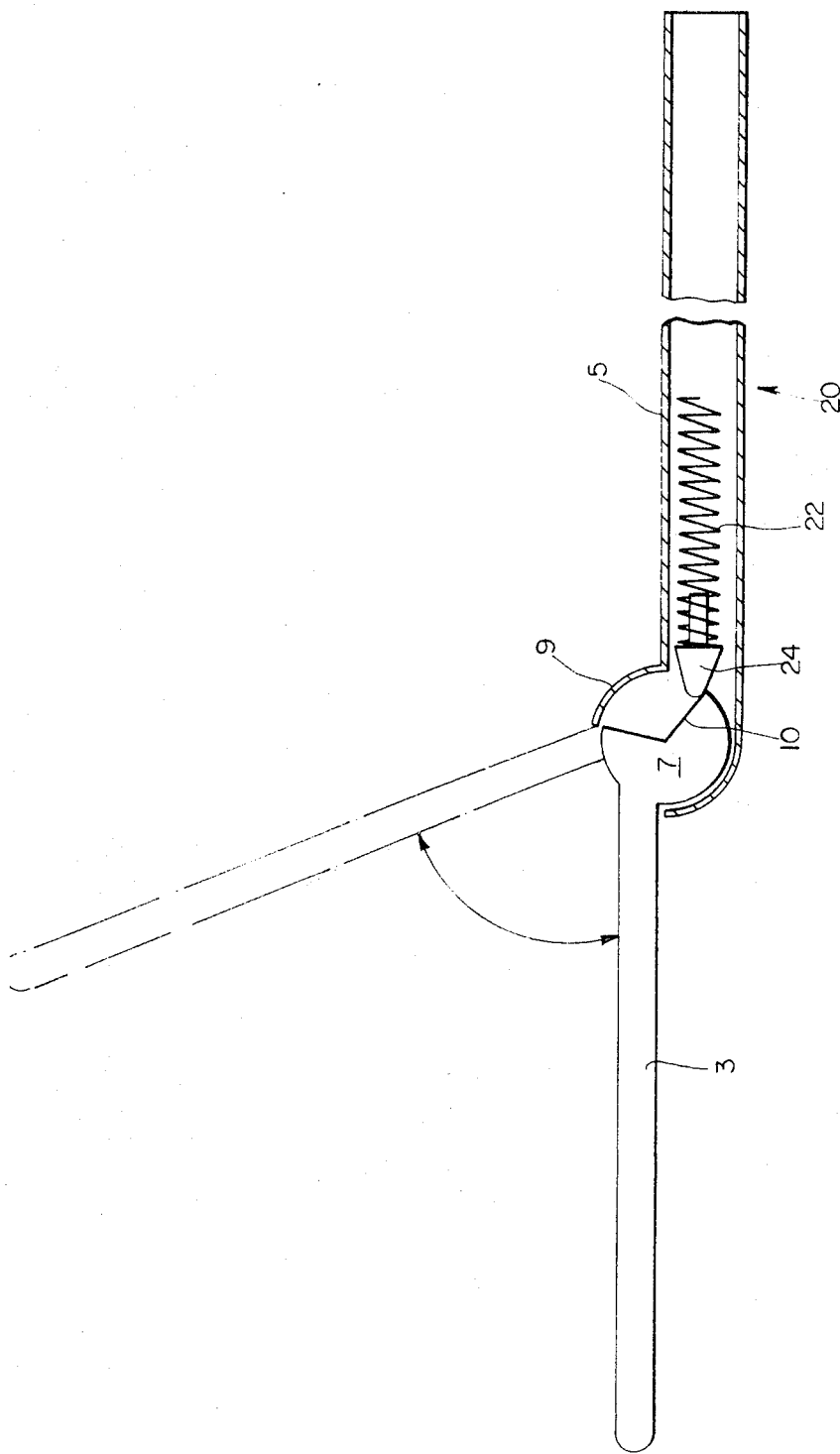
FIG. 2 is a perspective view of one upper and one lower strut assembly having a strut broken away to show the adjustable spring-loaded means mounted therein.
Figure 3:
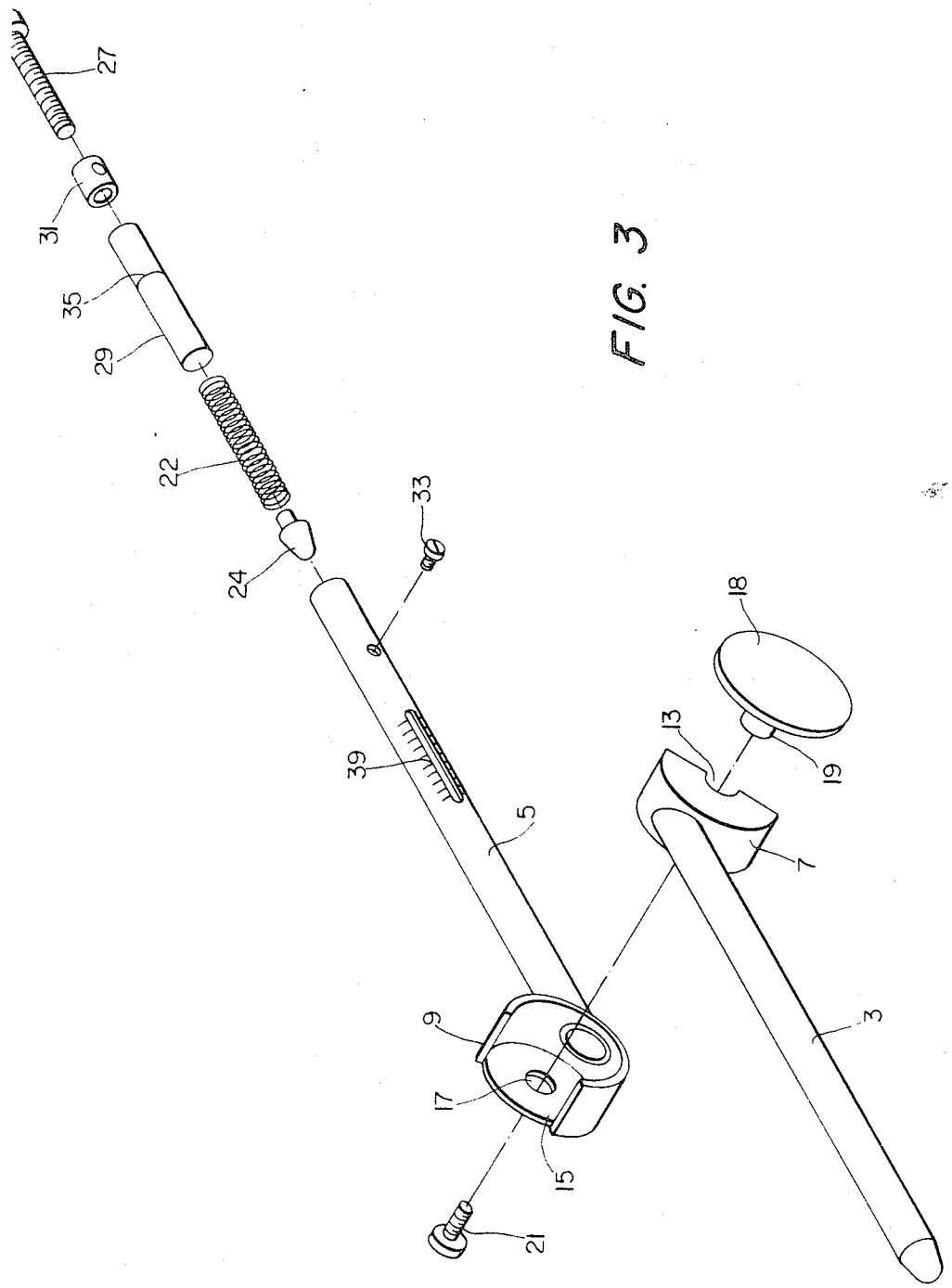
FIG. 3 is a perspective, exploded view of the splint device of the invention.

Referring to FIGS. 1-3, an adjustable splint device 1 is comprised of lower struts 3 and 3a and upper struts 5 and 5a. Lower strut 3 contains a rounded head portion 7 and upper strut 5 contains a socket head portion 9 which receives head portion 7 for pivotable engagement therewith. Rounded head portion 7 is cut away to define a cam surface 10 and is provided with an axial surface recess 13. A first surface plate 15 having a screw hole 17 covers one side of the combined head portions 7-9 and a second plate member 18 having a threaded protruding member 19 (see FIG. 3) covers the other half of the combined head portion 7-9. When surface plate member 18 is positioned over the combined head portion 7-9 protruding member 19 projects through the axial circular recess 13 and receives a screw 21 through screw hole 17. Lower strut 3a and upper strut 5a are similarly pivotably connected by corresponding members bearing like numbers but carrying the distinguishing suffix "a".

The lower and upper struts may be constructed of any material of sufficient strength such as plastic, metal, wood and the like. Particularly preferred are struts made of stainless steel metal. At least one of the struts should be at least partially hollow so as to house therein the adjustable spring mechanism of the invention. Most advantageously, all of the struts are tubular in construction so as to provide a lightweight product and if desired each of the struts 3, 3a, 5, and 5a can be comprised of two telescoping portions (not shown) so as to permit lengthening or shortening of the struts. Such a telescoping feature provides a splint which can be adjusted to several different lengths allowing the splint to fit a greater number of individuals.

The adjustable spring-loaded mechanism designated generally as 20 may be provided in either the lower or the upper struts. Preferably, only the lower struts 3 and 3a are provided with the adjustable spring mechanism.

The adjustable spring mechanism 20 is comprised of a spring 22 to which is attached a nose element 24 that bears on cam surface 10. Coil or clock springs are generally preferred but in some instances leaf springs are advantageously employed, particularly in small devices such as finger, elbow or wrist splints. An adjustable screw means indicated generally as 25 abuts the other end of the spring 22 and produces a quantifiable force which tends to approximate, i.e. bring together the lower strut 3 with the upper strut 5 and lower strut 3a with upper strut 5a. As maximum flexion is approached, tension is created in the compression coiled spring 22. The adjustable screw means 25 is comprised of an "Allen" head screw or slotted head screw 27 threaded to a spring-abutting member 29. The "Allen" head screw is fixed within upper strut 5 by screw 33. The "Allen" head screw 27 receives and is turned by an "Allen" socket wrench 32 (see FIG. 1) whereas a slotted head screw is adjustable with a conventional screwdriver blade. The turning of the screw creates greater compression of spring 22 thereby exerting greater force on the cam surface 10 of the lower strut 3 to exert a one way tension. The tension capability of the spring mechanism can range from 0 pounds tension to 10 pounds of tension and the tension exerted by the spring can be varied at any point of joint range of motion, say from 60° flexion to 0° flexion of the joint. The spring mechanism can be calibrated to exert this range of tension. The calibration can be effected by providing spring-abutting member 29 with a poundage indicator line 35 and a calibration scale 37 about the upper strut 5 which scale has a slot 39 thru which the poundage indicator 35 is visible.

While the preferred adjustable biasing means of the invention is a spring means such as described, equivalent biasing means such as air or hydraulic powered biasing means will readily come to the mind of those skilled in this art.

Any suitable means can be utilized to secure pivotably mounted struts 3 and 5 and pivotably mounted struts 3a and 5a to the limb so that they lie lateral to the joint with the axis of rotation coinciding as closely as possible to the axis of rotation of the joint. As shown in the figures, the securing means comprise a distal cuff 41 attached to and extending between lower strut 3a and lower strut 3 and approximal cuff 43 attached to and extending between upper strut 5a and upper strut 5. The length of the distal cuff 41 and approximal cuff 43 is of sufficient distance to comfortably accomodate the limb parts distal and proximal to the limb joint. An overlying flap 45 is attached at one end to lower strut 3a and contains on its undersurface an attaching means such as velcro hooks 46 by which the flap can wrap about the distal portion of the limb and be secured to the velcro loops 47 on the outersurface of the distal cuff wrapped about lower strut 3. Proximal cuff 43 is secured to upper strut 5a and 5 and contains two separate flaps 49 and 51 each containing on their underside velcro attaching loops 53 and 55, respectively. The flaps 49 and 51 are of sufficient length to extend over and secure the limb portion lying in proximal cuff 43 by attachment to the velcro loops receiving areas 57 and 59 provided on the proximal cuff 43 about the upper strut 5.

It should be understood that a single combined strut, such as lower strut 3 pivotably connected to upper strut 5, can alone be utilized as a splint device by securing same by suitable means to the lateral side of the limb to be treated. Again, any suitable means for strapping or securing the splint device of the invention can be used, for example, by distal and proximal cuffs of sufficient lengths to wrap around the distal and proximal portions of the limb being treated. The straps 45, 49 and 51 as well as the cuffs 41 and 43 can be secured to the struts in any suitable manner as by sewing, tying, etc.

Figure 4:
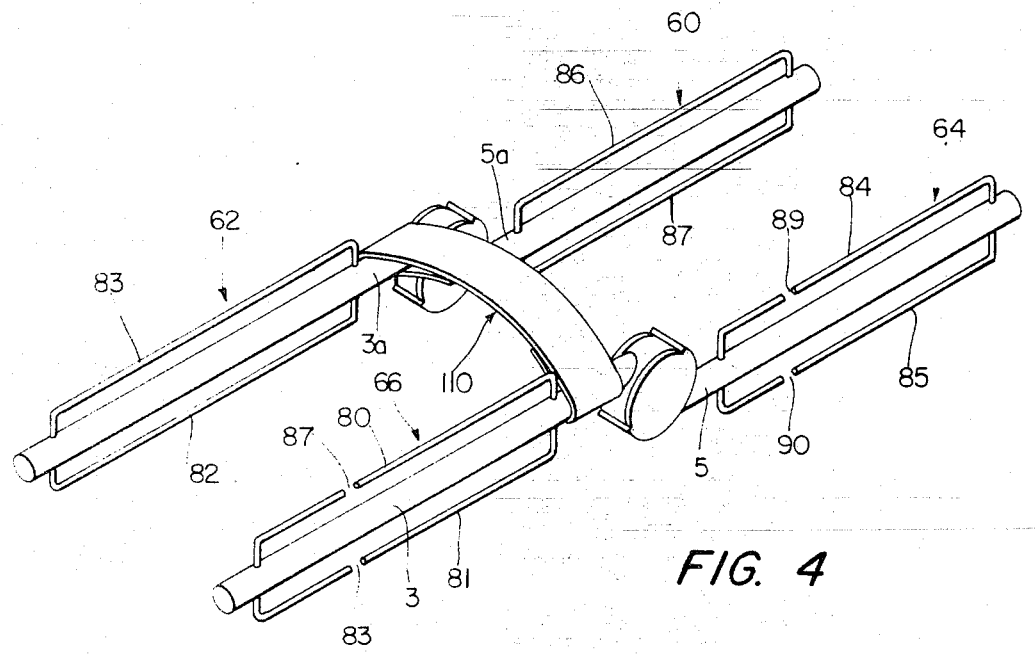
FIG. 4 is a perspective view of the splint device provided with a "break apart" wire assembly for mounting of the means by which the device is secured to the limb.

To facilitate the attachment of the cuffs and straps, however, it is preferred that wire assemblies, designated generally in FIG. 4 as 60, 62, 64 and 66, be fastened as by welding to struts 5, 5a and 3 and 3a, respectively. The wire assembly 62 is comprised of an upper thin wire portion 83 and a thin wire lower portion 82, each of which wire assembly portions extend from one end of strut 3a to the other. Similarly, wire assembly 60 is comprised of an upper thin wire portion 86 and a lower wire portion 87. Wire assemblies 64 and 66 differ from wire assemblies 60 and 62 in being of the "break apart" type as will be explained below so as to facilitate insertion and removal of the cuffs or straps for cleaning, replacing, etc. Thus, wire assembly 66 is comprised of an upper thin wire portion 80 and a lower thin wire portion 81 both of which are broken at 87 and 88, respectively, so that the wire can be pulled apart slightly when the cuff or straps are to be attached or removed. Similarly, wire assembly 64 is comprised of a thin upper wire section 84 and a thin lower wire section 85 both of which are broken at 89 and 90, respectively.

When the adjustable splint is to be used for extension of a joint, a strap 110 is provided between struts 3 and 3a. Strap 110 is important in this application in order to maintain optimal alignment of the upper and lower struts along the parallel of the limb part proximal and distal to the joint. Strap 110 also helps maintain the axis of rotation of the splint joint assembly more coincident with the axis of rotation of the body joint to which the splint is being applied.

Figure 5:
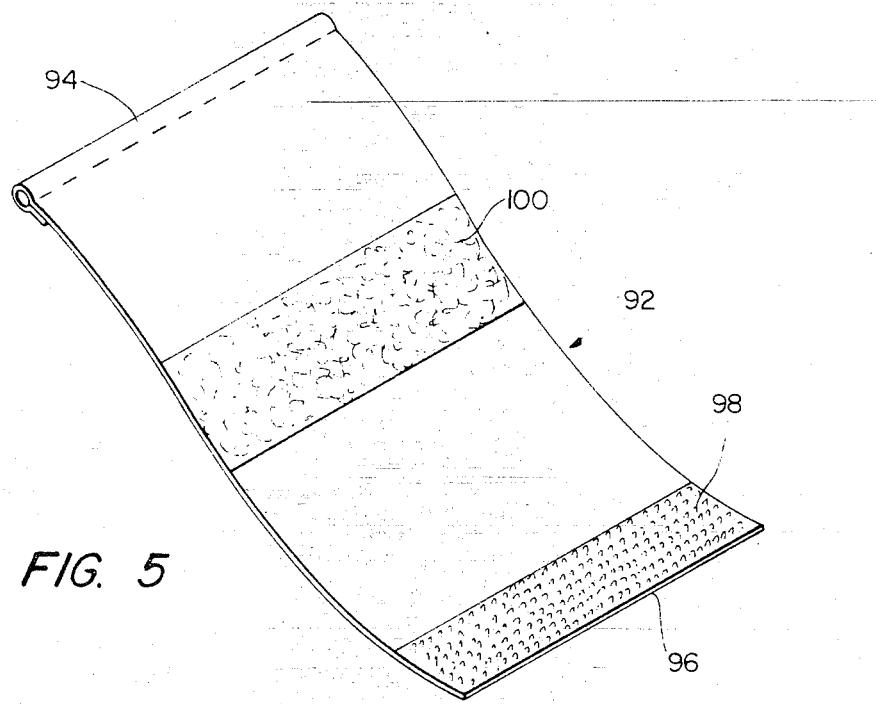
FIG. 5 is a cuff designed for attachment to the wire assembly shown in FIG. 4.

Attachment of cuff 92, provided with velcro hooks section 98 and a velcro loop section 100 as shown in FIG. 5, to the wire assemblies shown in FIG. 4 may then be conducted in the following manner:

Loop end section 94 of cuff 92 is put on wire portion 80 via break 87 with the velcro hooks section 98 and velcro loop section 100 facing upward. Edge 96 is taken over the limb and fed through and under wire portion 83 of wire assembly 62, over wire section 80, and then put back on itself whereby velcro hooks 98 adhere to velcro loops 100. This secures one of the four cuffs needed to fix the splint assembly to a limb about a joint. A cuff is attached to wire sections 84 and 86 in a similar manner. The same procedure is used to attach cuffs or straps to the wire sections 81-82 and wire sections 85-87 but in this case the velcro hooks section 98 and velcro loops section 100 are facing downward when the loop end section is put on the "break apart" wire.

Where but a single assembly of an upper and lower strut is to be used as the splint the respective cuffs and straps is to be used as the splint, the respective cuffs and straps are provided near their ends with suitable securing means such as velcro hooks and loops. It should be understood that while the securing means are shown to be velcro closures other alternative closures, such as snaps and the like can be provided the straps and cuffs.

The unique characteristics of the adjustable spring-loaded mechanism of the present invention is that it allows for adjustment of quantifiable force on an extremity acting across the body joint from 0 foot poundage up to the maximum foot poundage at various body joint ranges.

As an example of a particular case in which the adjustable splint for flexion of a joint might be used, one may consider an extension contracture, i.e. loss of ability to flex the joint through the normal range of motion, of any particular body joint such as the knee, elbow, wrist, fingers, etc. For simplicity the knee joint will be used.

In a knee extension contracture, whether the contracture is of a muscle or joint type, the individual may be able to flex the knee to 45° and no further. Applying the adjustable splint for flexion would be useful in that a force would be exerted on the body parts proximal and distal to the knee which would tend to approximate the calf to the posterior thigh. The force exerted by the splint would be adjustable from 0 foot pounds of torque across the knee joint to upward torque of whatever tension capability the particular spring being used would have. Surmising a reasonable force would be to have an upper limit of 10–20 foot pounds acting at mid calf and/or mid thigh. The exact tension desired would be determined by factors such as patient tolerance, type and age of the contracture, skin compliance, diagnosis, etc.

Once the beginning tension and duration of splint application is determined, progression of the tension and duration can be accomplished by simple adjustment of the head screw 27 and increasing time, respectively.

A unique feature of this device in the present application to the knee, and to any body joint, is the ability of this device to allow graduated, quantified, adjustable tension with the ability to relax the stretch across the joint by extending the knee away from the limit of flexion. This will allow the tissue being stretched to have a rest period while not disturbing the adjustment of the spring tension and without having to remove the splint. In order to relieve the pressure on the contractured tissues, one merely has to overcome, by any means, the tension in the splint and extend the joint to a comfortable posture. Once a short rest is achieved, the splint may again exert its tension against the contractured tissue to help accomplish a greater degree of flexion in the joint. In the case of a knee extension contracture, flexion would advance from the point of contracture, say 45° flexion, to the upper theoretical limits of flexion which, binding any other negating factors, would be 135°–150°. Time necessary to accomplish the optimal result using this splint would vary depending on many factors, some of which are the patient's diagnosis, age of patient, age of the contracture and tolerance of the patient.

While the features of this invention have been disclosed with reference to the specific embodiments described therein, it is to be understood that various modifications may be made in the construction without departing from the scope of the invention as defined in the appended claims.

It is claimed:

1. An adjustable splint assembly comprising a lower strut, an upper strut pivotably connected to said lower strut, one of said struts having at one end thereof a pivotably mounted head portion including a cam surface, the other of said struts comprising a tubular member having a longitudinal bore therein, adjustable biasing means located within the longitudinal bore in said tubular member and comprising a camming element located in said bore at one end of said tubular member and adapted to engage said cam surface of the head portion of the said one strut, spring means located within said bore for exerting a force on said camming member so as to bias said camming member into engagement with said cam surface of said head portion thereby to apply a quantifiable force tending to approximate said upper and lower struts, an adjustment means located at the other end of said tubular member for enabling the force exerted by said spring means on said camming element to be adjusted from the said other end of said tubular member, measuring means associated with said adjustment means for indicating the force exerted by said spring means, and means for securing said splint assembly to a limb.

2. An adjustable splint assembly as claimed in claim 1 including a strap means adjacent said pivotably mounted head portion attached to and extending between at least one pair of struts for maintaining alignment of the upper and lower struts along the parallel of the limb proximal and distal to the joint.

3. An adjustable splint assembly as claimed in claim 1 wherein said measuring means comprises a scale located on said tubular member and indication means associated with said adjustment means for cooperating with said scale to provide an indication of the force exerted by said spring means.

4. An adjustable splint assembly as claimed in claim 3 wherein said adjustment means includes an abutment member located within said bore which abuts said spring means, and wherein said scale is located along a slot in said tubular member and said indication means comprises an indicia located on said abutment member and viewable through said slot.

5. An adjustable splint assembly as claimed in claim 4 wherein said other strut includes a generally cylindrical chamber at the pivot end thereof which communicates with said longitudinal bore and which includes a slot therein through which the head portion of said one strut extends, said head portion including an outer part-cylindrical side wall which engages the inner wall of said chamber, and the cam surface of said head portion extending between said side wall and an inner wall of said head portion.

6. An adjustable splint assembly as claimed in claim 1 wherein said spring means comprises a coil spring and wherein said adjustment means comprises a member which abuts one end of said coil spring and a screw member threadably engaged in a threaded member fixed within said longitudinal bore in said tubular member, one end of said screw member having a rotatable head and the other end of said screw member being engagable with the spring abuting member.

7. An adjustable splint assembly as claimed in claim 2 wherein said adjustment means includes a screw member located within said bore in said tubular member, said measuring means including a scale formed on said tubular member and an indicator member which cooperates with said scale and which is moveable responsive to rotation of said screw member.

* * * * *